United States Patent
Sakane et al.

[11] Patent Number: 5,104,866
[45] Date of Patent: Apr. 14, 1992

[54] WATER-SOLUBLE ANTIBIOTIC COMPOSITION AND WATER-SOLUBLE SALTS OF CEPHEM COMPOUNDS

[75] Inventors: Kazuo Sakane, Kawanishi; Nobuyoshi Yasuda, Nishinomiya; Shintaro Nishimura, Settsu, all of Japan

[73] Assignee: Fujisawa Pharmaceutical Company, Ltd., Osaka, Japan

[21] Appl. No.: 560,229

[22] Filed: Jul. 25, 1990

Related U.S. Application Data

[63] Continuation of Ser. No. 228,450, Aug. 5, 1988, abandoned.

[30] Foreign Application Priority Data

| Aug. 10, 1987 | [GB] | United Kingdom | 8718905 |
| Sep. 14, 1987 | [GB] | United Kingdom | 8721567 |
| Oct. 26, 1987 | [GB] | United Kingdom | 8725051 |
| Dec. 18, 1987 | [GB] | United Kingdom | 8729574 |
| Jan. 22, 1988 | [GB] | United Kingdom | 8801423 |

[51] Int. Cl.$^5$ ............... C07D 501/20; A61K 31/545
[52] U.S. Cl. ................................. 514/206; 540/225
[58] Field of Search .................... 540/222, 227, 225

[56] References Cited

U.S. PATENT DOCUMENTS

| 4,161,527 | 7/1979 | Ishizuka et al. | 424/246 |
| 4,241,057 | 12/1980 | Ishizuka et al. | 514/206 |
| 4,331,665 | 5/1982 | Teraji et al. | 540/225 |
| 4,332,800 | 6/1982 | Teraji et al. | 424/246 |
| 4,338,313 | 7/1982 | Teraji et al. | 424/246 |
| 4,390,534 | 6/1983 | Teraji et al. | 424/246 |
| 4,563,449 | 1/1986 | Teraji et al. | 514/203 |
| 4,582,830 | 4/1986 | Richardson | 514/203 |
| 4,624,948 | 11/1986 | Durckheimer | 514/203 |
| 4,845,087 | 7/1989 | Lattrell et al. | 540/222 |

FOREIGN PATENT DOCUMENTS 0188255 7/1986 European Pat. Off.
2445833 8/1980 France.

*Primary Examiner*—Nicholas S. Rizzo
*Attorney, Agent, or Firm*—Oblon, Spivak, McClelland, Maier & Neustadt

[57] ABSTRACT

A water-soluble antibiotic composition which comprises crystals of a cephem compound of the following formula:

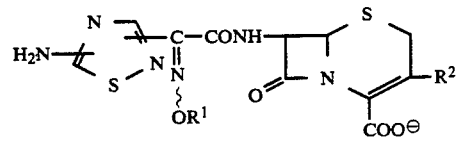

wherein $R^1$ is a residue of an aliphatic hydrocarbon which may have suitable substituent(s), and
$R^2$ is a heteronio (lower)alkyl, or an acid addition salt thereof, and a pharmaceutically acceptable carbonic acid salt.
And a salt of new cephem compound derived from the above-mentioned cephem compound.

15 Claims, No Drawings

WATER-SOLUBLE ANTIBIOTIC COMPOSITION AND WATER-SOLUBLE SALTS OF CEPHEM COMPOUNDS

This application is a continuation of application Ser. No. 07/228,450, filed on Aug. 5, 1988, now abandoned.

This invention relates to a water-soluble antibiotic composition and salts of new cephem compounds.

More particularly, this invention relates to a water-soluble antibiotic composition which comprises crystals of a cephem compound and a pharmaceutically acceptable carbonic acid salt, and to a process for preparation thereof.

Further, this invention relates to salts of new cephem compounds, to a process for preparation thereof, to a pharmaceutical composition comprising the same and to a use thereof.

In the past, many of the compound, which is included within the scope of the following chemical formula (II), were prepared, for example, in European Patent Publication Nos. 0027599 and 0188255.

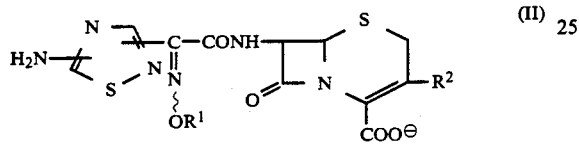
(II)

wherein $R^1$ is a residue of an aliphatic hydrocarbon which may have suitable substituent(s), and $R^2$ is a heteronio(lower)alkyl.

The above cephem compound itself or its acid addition salt exhibits high antibacterial activity and inhibits the growth of a wide variety of pathogenic bacteria including Gram-positive and Gram-negative bacteria. However, the poor solubility in water of its crystalline state and the poor stability of its amorphous solid state have been preventing its development as an injectable medicament.

In order to overcome such defects, the inventors of the present invention intensively studied and as a result thereof they have found that the solubility of the crystals of the cephem compound (II) or its acid addition salt in water was remarkably improved by making said crystals a composition with a carbonic acid salt, that is, dissolving the crystals of the cephem compound (II) in water in the presence of a carbonic acid salt.

Further, the inventors continued their study and have found the fact that in an aqueous solution of said composition, salts of the new cephem compounds derived from the cephem compound (II)are prepared, which are higher soluble in water.

Accordingly, the first object of the present invention is to provide a water-soluble antibiotic composition, which comprises crystals of the cephem compound and a pharmaceutically acceptable carbonic acid salt.

The second object of the present invention is to provide a process for preparation of the above antibiotic composition.

The third object of the present invention is to provide salts of the water-soluble new cephem compounds, which are active against a number of pathogenic microorganisms.

The fourth object of the present invention is to provide a process for preparing the salts of the new cephem compounds.

The fifth object of the present invention is to provide a pharmaceutical composition comprising the salts of the new cephem compounds.

And, the sixth object of the present invention is to provide a use of the salts of the new cephem compounds for treating infectious diseases caused by pathogenic bacteria in human or animals.

With regard to the cephem compound (II) and salts (I) of the new cephem compounds mentioned below, it is to be understood that all of said compounds include syn isomer, anti isomer and a mixture thereof And, the syn isomer thereof means one geometrical isomer having the group represented by the following formula:

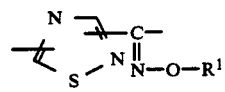

(wherein $R^1$ is as defined below) and the anti isomer means the other geometrical isomer having the group of the formula:

(wherein $R^1$ is as defined below), and in the present invention, the syn isomer is preferable.

WATER-SOLUBLE ANTIBIOTIC COMPOSITION

The water-soluble antibiotic composition of the present invention is novel and comprises crystals of the cephem compound of the following chemical formula:

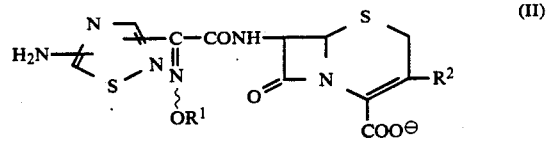
(II)

wherein $R^1$ and $R^2$ are each as defined above, or an acid addition salt thereof, and a pharmaceutically acceptable carbonic acid salt.

With regard to the definitions of the symbols $R^1$ and $R^2$ used in the cephem compound (II), suitable examples and illustration thereof which the present invention intends to include within the scope are explained in detail as follows.

The term "lower" is used to intend a group having 1 to 6 carbon atom(s), unless otherwise provided.

Suitable aliphatic hydrocarbon may include cyclic or acyclic aliphatic hydrocarbon, such as lower alkyl, which may include straight or branched one having 1 to 6 carbon atom(s), such as methyl, ethyl, propyl, isopropyl, butyl, isobutyl, sec-butyl, tert-butyl, pentyl, tert-pentyl, hexyl, etc., preferably one having 1 to 4 carbon atom(s); lower alkenyl, which may include straight or branched one having 2 to 6 carbon atoms, such as vinyl, allyl, 1-propenyl, 2-methylallyl, 2-butenyl, 2-pentenyl, 5-hexenyl, etc.

The residue of an aliphatic hydrocarbon thus defined may have one or more, preferably, one to two suitable substituents. Such suitable substituent(s) may be a conventional one used in the cephalosporin field, such as carboxy, halogen (e.g. fluorine, chlorine, bromine, etc.), cyano, amino, hydroxy, and the like.

Suitable heteronio moiety of the heteronio(lower)alkyl group may be a conventional one, which is used as a substituent at the 3rd position in the cephalosporin field. More preferably, it may include 5- to 10-membered, mono or bicyclic heterocyclic group containing quarternary nitrogen atom, which may have one or more suitable substituent(s) such as carbamoyl, and the like.

Suitable example of the heteronio group thus defined may be pyridinio, quinuclidinio or a group or the formula:

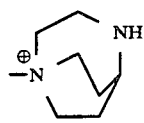

each of which may have carbamoyl.

Suitable lower alkyl moiety of the heteronio(lower-)alkyl may be a straight or branched one having 1 to 6 carbon atoms(s) such as those exemplified above.

Suitable acid addition salt of the cephem compound (II) is a conventional non-toxic, hemi-, mono- or di-pharmaceutically acceptable acid addition salt formed by the cephem compound (II) and mono- or poly-basic acid and may include an inorganic acid addition salt (e.g., hydrochloride, sulfate, etc.) or an organic acid addition salt (e.g. acetate, etc.) and the like, in which hydrochloride and sulfate is the most preferable.

The cephem compound (II) or an acid addition salt thereof may be in a form of its hydrate.

Suitable hydrate of the compound (II) or an acid addition salt thereof may include monohydrate, dihydrate and so on, which is usable for the preparation of the water-soluble antibiotic composition of the present invention. And more preferable one is the dihydrate of it.

Suitable pharmaceutically acceptable carbonic acid salt is alkaline metal hydrogencarbonate (e.g., sodium hydrogencarbonate, potassium hydrogencarbonate, etc.), alkaline metal carbonate (e.g., sodium carbonate, potassium carbonate, etc.), ammonium carbonate, ammonium hydrogencarbonate, and the like.

The proportion of the pharmaceutically acceptable carbonic acid salt relative to the cephem compound (II) or an acid addition salt thereof is not particularly restrictive, and can be selected from any one which is capable of easily dissolving the cephem compound (II) and which does not give bad influence on patients.

The preferable proportion of the pharmaceutically acceptable carbonic acid salt to the cephem compound (II) or an acid addition salt thereof is 1:5 to 10:1 by mole ratio, which is selected depending on the kinds of the carbonic acid, the cephem compound (II) and the acid addition salt thereof.

Particularly, the suitable proportion of the pharmaceutically acceptable carbonic acid salt relative to the acid addition salt of the cephem compound (II) is such that the ratio of the pharmaceutically acceptable carbonic acid salt to the acid addition salt of the cephem compound (II) is substantially within the range of 0.5:1 to 4:1 equivalents and preferably 1:1 to 3:1 equivalents.

It follows that the monoacidic base such as sodium hydrogencarbonate is normally used in a proportion of 0.5 to 4 moles, preferably 1 to 2 moles per mole of the monoacid addition salt of the cephem compound (II) in case that the basicity of the acid is 1. And that the diacidic base such as sodium carbonate is normally employed within the range of 0.25 to 2 moles, preferably 0.5 to 1 moles per mole of the monoacid addition salt of the cephem compound (II) in case that the basicity of the acid is 1.

The antibiotic composition of this invention is produced by admixing the crystals of the cephem compound (II) or its acid addition salt with a pharmaceutically acceptable carbonic acid salt by a conventional means. In this admixing procedure, there may also be incorporated certain other known pharmacuetical additives including local anaesthetics such as lidocaine hydrochloride, mepivacaine hydrochloride and the like. The composition thus produced is usually aseptically packed into vials.

While the dosage of the active ingredient of the water-soluble antibiotic composition of the present invention will vary depending upon the age and condition of the patient, an average single dose of about 10 mg, 50 mg, 100 mg, 250 mg, 500 mg and 1000 mg of the compound (II) on an anhydrous compound (II) basis according to the present invention was proved to be effective for treating infectious diseases caused by pathogenic microorganisms. In general, amounts between 1 mg/body and about 6,000 mg/body or even more may be administered per day.

In the present water-soluble antibiotic composition, the acid addition salt of the cephem compound (II) is more preferable for a component of the present water-soluble antibiotic composition, because the dissolution rate of the composition comprising the acid addition salt of the cephem compounds (II) is faster than that of composition comprising the corresponding free cephem compound (II).

The cephem compound (II) or a salt thereof and their crystals can be prepared according to the methods described in the preparation mentioned below of this specification or in the before-mentioned, known European Patent Publications.

SALTS OF NEW CEPHEM COMPOUNDS

During the inventors' investigation on the water-soluble antibiotic composition mentioned above, they found that some type of salts of the new cephem compounds derived from the cephem compound (II) is formed in an aqueous solution of said composition. And as a result of their continuous investigation, the inventors have succeeded in preparing water-soluble salts of new cephem compounds of the present invention.

The salts (I) of new cephem compounds can be represented as follows.

Salts (I) of the new cephem compound comprising cation(s) and anion of the formula:

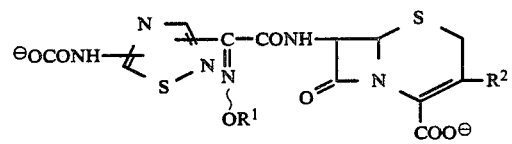

wherein $R^1$ and $R^2$ are each as defined above.

With regard to the definitions of the symbols $R^1$ and $R^2$, there may be exemplified the same ones as those mentioned for the cephem compound (II).

The salts (I) of the new cephem compounds can be prepared by a process which is illustrated in the following scheme.

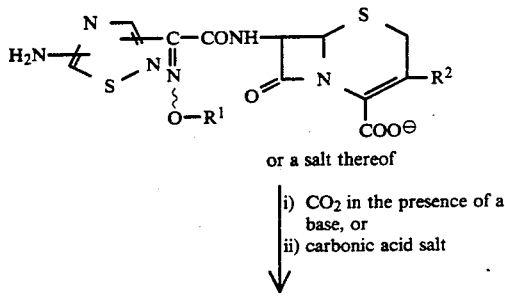

or a salt thereof i) $CO_2$ in the presence of a base, or
ii) carbonic acid salt

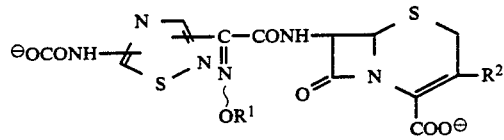

salts (I) of the new cephem compounds comprising cation(s) and anion of the formula:

wherein $R^1$ and $R^2$ are each as defined above.

Suitable cation(s) may be pharmaceutically acceptable cation(s), such as an alkaline metal cation(s) (e.g., sodium cation, potassium cation, etc.), an alkaline earth metal cation(s) (e.g., calcium cation, magnesium cation, etc.), ammonium ion(s), etc., and the most suitable pharmaceutically acceptable cation is sodium cation.

In case the cation is a multivalent one, it normally forms a salt with an equivalent number of anions to the valency of the cation.

Further it is to be noted that the various type of salts can be formed due to the presence of two carboxylato ions in the molecule of the object salts (I). When one of the two carboxylato ions forms a salt with one cation, the other carboxylato ion may form an intramolecular salt with a heteronio ion of $R^2$.

Still further, the two carboxylato ions may form salts with cations simultaneously, and in this case, the heteronio ion forms a salt with an anion from a base being used in a process of its preparation.

The process for preparing the object salts (I) is explained in detail in the following.

The object salts (I) can be prepared by reacting the compound (II) or a salt thereof with carbon dioxide in the presence of base, or with carbonic acid salt.

Suitable salt of the starting compound (II) are conventional pharmaceutically acceptable non-toxic salt and may include an inorganic salt, for example, a metal salt such as an alkaline metal salt (e.g., sodium salt, potassium salt, etc.) and an alkaline earth metal salt (e.g., calcium salt, magnesium salt, etc.), ammonium salt etc.; an organic salt for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt, dibenzylethylenediamine salt, etc.) etc.; an organic carboxylic or sulfonic acid salt (e.g., formate, acetate, maleate, tartrate, methanesulfonate, benzenesulfonate, toluenesulfonate, etc.); an inorganic acid salt (e.g., hydrochloride, hydrobromide, sulfate, phosphate, etc.); a salt with a basic or acidic amino acid (e.g., arginine, aspartic acid, glutamic acid, lysine, etc.) and the like.

Carbon dioxide can be supplied by various states, such as dry ice, carbonic acid gas, etc.

In this reaction, the cation(s) may be pharmaceutically acceptable one(s) supplied by a base used in a preparation of the object salts (I), and preferred base is an alkaline metal hydroxide (e.g. sodium hydroxide, potassium hydroxide, etc.), an alkaline earth metal hydroxide (e.g., magnesium dihydroxide, calcium dihydroxide, etc.), the above alkaline or alkaline earth metal salt of a weak acid (e.g., sodium hydrogencarbonate, potassium hydrogencarbonate, sodium carbonate, calcium carbonate, etc.), or any other base which is capable of supplying pharmaceutically acceptable cation(s).

Suitable carbonic acid salt used in this reaction may be the same as those given for the pharmaceutically acceptable carbonic acid salt in the water-soluble antibiotic composition.

The reaction is usually carried out in a conventional solvent such as water, acetone, dioxane, acetonitrile, chloroform, carbon tetrachloride, dichloromethane, dichloroethane, tetrahydrofuran, ethyl acetate, N,N-dimethylformamide, dimethylsulfoxide or any other organic solvent which does not adversely influence the reaction. Among the solvents, hydrophilic solvents may be used in a mixture with water.

The reaction temperature is not critical and the reaction is usually carried out under cooling to warming.

The object salts (I) of the present invention are novel compounds which exhibit high antibacterial activity and inhibit the growth of a wide variety of pathogenic microorganisms including Gram-positive and Gram-negative bacteria and further, possess higher solubilities in water as compared with the corresponding free aminothiadiazol compounds, and are therefore useful as antimicrobial agents. For therapeutic purpose, the salts according to the present invention can be used in the form of conventional pharmaceutical preparation which contain said salts, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives, such as lactose, magnesium stearate, terra alba, sucrose, corn starch, talc, gelatin, agar, pectin, peanut oil, olive oil, cacao butter, ethylene glycol and the like.

While the dosage of the salts will vary depending upon the age and condition of the patient, an average single dose of about 10 mg, 50 mg, 100 mg, 250 mg, 500 mg and 1000 mg of the salts according to the present invention was proved to be effective for treating infectious diseases caused by pathogenic microorganisms. In general, amounts between 1 mg/body and about 6,000 mg/body or even more may be administered per day.

Preferred embodiments of the object salts (I) and the cephem compound (II) of the present invention are as follows.

Cation is a sodium cation;

$R^1$ is $(C_1-C_4)$alkyl (more preferably methyl, ethyl or propyl) or $(C_2-C_4)$alkenyl (more preferably allyl);

$R^2$ is a group of the formula;

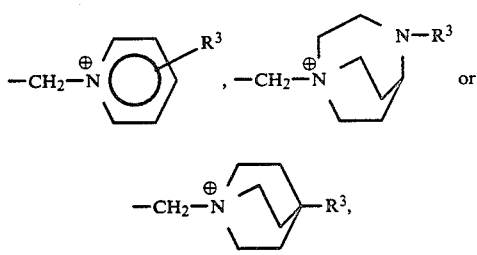

and $R^3$ is hydrogen or carbamoyl.

Now in order to show the utility of the composition of the present invention, dissolution tests for the various types of the compositions were conducted, the results of which are shown in the following.

In the Dissolution Tests, Preparations and Examples mentioned hereinbelow,

Compound A means:
Crystal of 7-[2-allyloxyimino-2-(5-amino-1,2,4-thiadiazol-3-yl)acetamido]-3-(1-pyridinio)methyl-3-cephem-4-carboxylate hydrochloride dihydrate (syn isomer), Compound B means:
Crystal of 7-[2-allyloxyimino-2-(5-amino-1,2,4-thiadiazol-3-yl)acetamido]-3-(1-pyridinio)methyl-3-cephem-4-carboxylate hydrochloride (syn isomer), Compound C means:
Crystal of 7-[2-allyloxyimino-2-(5-amino-1,2,4-thiadiazol-3-yl)acetamido]-3-(1-pyridinio)methyl-3-cephem-4-carboxylate (syn isomer), Compound D means:
Crystal of 7-[2-(5-amino-1,2,4-thiadiazol-3-yl)-2-methoxyiminoacetamido]-3-(1-pyridinio)methyl-3-cephem-4-carboxylate sulfate (syn isomer), Compound E means:
Crystal of 7-[2-(5-amino-1,2,4-thiadiazol-3-yl)-2-methoxyiminoacetamido]-3-(1-pyridinio)methyl-3-cephem-4-carboxylate (syn isomer), Compound F means:
Crystal of 7-[2-allyloxyimino-2-(5-amino-1,2,4-thiadiazol-3-yl)acetamido]-3-(1-pyridinio)methyl-3-cephem-4-carboxylate hemisulfate (syn isomer), and Compound G means:
Crystal of 7-[2-allyloxyimino-2-(5-amino-1,2,4-thiadiazol-3-yl)acetamido]-3-(1-pyridinio)methyl-3-cephem-4-carboxylate sulfate (syn isomer).

DISSOLUTION TESTS

Test Samples

The pharmaceutical preparations obtained according to Examples 1 to 11, which contain the following amounts of the Compounds A to E and carbonic acid salt, were used as Test Samples (1) to (11), respectively.

| Test Sample (1): | |
|---|---|
| Compound A | 50 mg |
| Sodium carbonate | 9.3 mg |
| Test Sample (2): | |
| Compound A | 50 mg |
| Sodium hydrogencarbonate | 7.3 mg |
| Test Sample (3): | |
| Compound A | 50 mg |
| Potassium carbonate | 12 mg |
| Test Sample (4): | |
| Compound A | 50 mg |
| Potassium hydrogencarbonate | 17.4 mg |
| Test Sample (5): | |
| Compound A | 50 mg |
| Sodium hydrogencarbonate | 14.6 mg |
| Test Sample (6): | |
| Compound A | 50 mg |
| Ammonium carbonate | 18.9 mg |
| Test Sample (7): | |
| Compound A | 50 mg |
| Ammonium hydrogencarbonate | 13.8 mg |
| Test Sample (8): | |
| Compound B | 50 mg |
| Sodium carbonate | 11.9 mg |
| Test Sample (9): | |
| Compound C | 50 mg |
| Sodium hydrogencarbonate | 8.4 mg |
| Test Sample (10): | |
| Compound D | 50 mg |
| Sodium hydrogencarbonate | 22 mg |
| Test Sample (11): | |
| Compound E | 50 mg |
| Sodium hydrogencarbonate | 8.8 mg |

As a comparison, the following reference samples were also tested.

| Reference Sample (1): | |
|---|---|
| Compound C | 50 mg |
| Reference Sample (2): | |
| Compound B | 50 mg |
| Reference Sample (3): | |
| Compound E | 50 mg |
| Reference Sample (4): | |
| Compound D | 50 mg |

Test Method

The velocity of dissolution of the test samples were observed after addition of distilled water into said test samples at ambient temperature, respectively.

Concentrations (w/v) of the cephem compound(II) in the dissolved test samples were provided in the parentheses.

TABLE 1

| | Volume of Distilled Water (ml) | Velocity of Dissolution (Concentration) |
|---|---|---|
| Test Sample (1) | 0.25 | ≦1 minute (20% w/v) |
| Test Sample (2) | 0.25 | ≦1 minute (20% w/v) |
| Test Sample (3) | 0.25 | ≦1 minute (20% w/v) |
| Test Sample (4) | 0.25 | ≦1 minute (100% w/v) |
| Test Sample (5) | 0.05 | ≦1 minute (20% w/v) |
| Test Sample (6) | 0.25 | ≦1 minute (20% w/v) |
| Test Sample (7) | 0.25 | ≦1 minute (20% w/v) |
| Test Sample (8) | 0.25 | ≦1 minute (20% w/v) |
| Test Sample (9) | 0.25 | ≦A few hours (20% w/v) |
| *1 Reference Sample (1) | 0.25 | Slightly soluble |

TABLE 1-continued

| | Volume of Distilled Water (ml) | Velocity of Dissolution (Concentration) |
|---|---|---|
| *2 Reference Sample (2) | 0.25 | Slightly soluble |

Note
*1: Maximum concentration of this sample dissolved in water was 4.07% (w/v).
*2: Maximum concentration of this sample dissolved in water was 8.28% (w/v).

TABLE 2

| | Volume of Distilled Water (ml) | Velocity of Dissolution (Concentration) |
|---|---|---|
| Test Sample (10) | 0.25 | ≦1 minute (20% w/v) |
| Test Sample (11) | 0.25 | ≦A few hours (20% w/v) |
| *3 Reference Sample (3) | 0.25 | Slightly soluble |
| *4 Reference Sample (4) | 0.25 | Slightly soluble |

Note
*3: Maximum concentration of this sample dissolved in water was 2% (w/v).
*4: Maximum concentration of this sample dissolved in water was 10% (w/v).

And, further, in order to show the utility of the salts(I) of new cephem compounds, with regard to a representative salt of this inventions, the test data on the in vitro anti-bacterial activity are shown in the following.

TEST SALT

Sodium 7-[2-allyloxyimino-2-(5-carboxylatoamino-1,2,4-thiadiazol-3-yl)acetamido]-3-(1-pyridinio)methyl-3-cephem-4-carboxylate (syn isomer).

TEST METHOD

In vitro antibacterial activity was determined by the two-fold agar-plate dilution method as described below.

One loopful of an overnight culture of test strain in Trypticase-soy broth ($10^6$ viable cells per ml) was streaked on heart infusion agar (HI-agar) containing graded concentrations of test salt, and minimal inhibitory concentration (MIC) was expressed in terms of μg/ml after incubation at 37° C. for 20 hours.

| Test Strains | Test Result MIC (μg/ml) Test salt |
|---|---|
| P. aeruginosa 26 | 0.390 |

The following Preparations and Examples are given for the purpose of illustrating the present invention.

PREPARATION 1

To a solution of 1,4-diazabicyclo[3.2.2]nonane (2.75 g) in a mixture of tetrahydrofuran (40 ml) and water (20 ml) was added potassium cyanate (2.65 g) at ambient temperature. The mixture was adjusted to pH 5.0 with concentrated hydrochloric acid and stirred at 50° C. for 40 minutes. The mixture was poured into 50% aqueous solution of potassium hydroxide. The resulted aqueous solution was extracted with chloroform. The extract was dried over anhydrous potassium carbonate and evaporated to dryness in vacuo. The crystalline residue was recrystallized from diethyl ether to give 4-carbamoyl-1,4-diazabicyclo[3.2.2]nonane (898.5 mg).
mp: 125° to 130° C.
IR (Nujol): 1640, 1585 cm$^{-1}$
NMR (CDCl$_3$, δ): 1.50–2.30 (4H, m), 2.90–3.40 (6H, m), 3.50–3.80 (2H, m), 4.05 (1H, m), 4.73 (2H, m)
Mass: m/z 169 (M$^+$)

PREPARATION 2

1) To a mixed solution of dichlorometahne (1000 ml) and tetrahydrofuran (200 ml) were added 2-(5-amino-1,2,4-thiadiazol-3-yl)-2-(methoxyimino)acetyl chloride (syn isomer) (64 g) and benzhydryl 7-amino-3-chloromethyl-3-cephem-4-carboxylate hydrochloride (100 g) at −15° C. The mixture was stirred at −15° C. for one hour. The reaction mixture was poured into ice-cooled water, and neutralized with sodium hydrogencarbonate. The organic layer was separated, dried over magnesium sulfate and evaporated in vacuo. The residue was triturated with diisopropyl ether to give benzhydryl 7-[2-(5-amino-1,2,4-thiadiazol-3-yl)-2-methoxyiminoacetamido]-3-chloromethyl-3-cephem-4-carboxylate (syn isomer) (130.5 g)
NMR (DMSO-d$_6$, δ): 3.2–3.8 (2H, m), 3.93 (3H, s), 4.43 (2H, s), 5.27 (1H, d, J=5 Hz), 5.97 (1H, dd, J=5 Hz, 8 Hz), 7.00 (1H, s), 7.20–7.70 (10H, m), 8.17 (2H, s), 9.70 (1H, d, J=8 Hz)

2) To a solution of benzhydryl 7-[2-(5-amino-1,2,4-thiadiazol-3-yl)-2-methoxyiminoacetamido]-3-chloromethyl-3-cephem-4-carboxylate (syn isomer) (3 g) in dichloromethane (6 ml) and anisole (3 ml) was added dropwise trifluoroacetic acid (6 ml) at 0° C. The mixture was stirred at 0° C. for two hours. The mixture was poured into a chilled mixture of diisopropyl ether and n-hexane (1:1, V/V). The precipitates were collected by filtration and dried under reduced pressure to give 7-[2-(5-amino-1,2,4-thiadiazol-3-yl)-2-methoxyiminoacetamido]-3-chloromethyl-3-cephem-4-carboxylic acid trifluoroacetate (syn isomer) (2.50 g).
IR (Nujol): 1770, 1630, 1600 cm$^{-1}$
NMR (DMSO-d$_6$, δ): 3.63 (2H, m), 3.93 (3H, s), 4.57 (2H, s), 5.18 (1H, d, J=5 Hz), 5.83 (1H, dd, J=5 Hz, 8 Hz), 8.10 (2H, broad s), 9.55 (1H, d, J=8 Hz)

PREPARATION 3

To a solution of 7-[2-(5-amino-1,2,4-thiadiazol-3-yl)-2-methoxyiminoacetamido]-3-chloromethyl-3-cephem-4-carboxylic acid trifluoroacetate (syn isomer) (1.03 g) in N,N-dimethylformamide (20 ml) was added 4-carbamoyl-1,4-diazabicyclo[3.2.2]nonane (800 mg) at 0° C. The mixture was stirred for 20 minutes at 0° C. The mixture was poured into ethyl acetate (150 ml). The precipitates were collected by filtration and dried under reduced pressure. The solid was dissolved in water (50 ml) and chromatographed on non-ionic adsorption resin "Diaion HP-20" (Trademark, maker; Mitsubishi Chemical Industries) (40 ml) eluting with 5% isopropyl alcohol in water. The desired fractions were collected and lyophilized to give 7-[2-(5-amino-1,2,4-thiadiazol-3-yl)-2-methoxyiminoacetamido]-3-[4-carbamoyl-1,4-diazabicyclo[3.2.2]nonan-1-ylio]methyl-3-cephem-4-carboxylate (syn isomer) (359 mg).
mp: 140° C. (dec.)
IR (Nujol): 1770, 1660, 1610 cm$^{-1}$
NMR (DMSO-d$_6$, δ): 2.70–4.50 (17H, m), 3.92 (3H, s), 5.15 (1H, d, J=5 Hz), 5.50–6.10 (3H, m), 8.10 (2H, s), 9.50 (1H, d, J=8 Hz)
Mass: m/z 566 (M$^{30}$)

PREPARATION 4

To a solution of 7-[2-(5-amino-1,2,4-thiadiazol-3-yl)-2-methoxyiminoacetamido]-3-[4-carbamoyl-1,4- diazabicyclo[3.2.2]nonan-1-ylio]methyl-3-cephem-4-carboxylate (syn isomer) (8.03 g) in water (8.03 ml) was added 2 N sulfuric acid (8.03 ml) at ambient temperature. The solution was allowed to stand for one hour. The colorless crystals were collected by filtration, washed with cooled water and acetone, and dried over phosphorus pentoxide to give colorless crystals of 7-[2-(5-amino-1,2,4-thiadiazol-3-yl)-2-methoxyiminoacetamido]-3-[4-carbamoyl-1,4-diazabicyclo[3.2.2]nonan-1-ylio]methyl-3-cephem-4-carboxylate sulfate (syn isomer) (6.18 g).

mp: 180° C. (dec.)

IR (Nujol): 1795, 1645, 1540 cm$^{-1}$

NMR (D$_2$O, δ): 2.05–2.70 (4H, m), 3.30–4.40 (13H, m), 4.10 (3H, s), 5.35 (1H, d, J=5 Hz), 5.85 (1H, d, J=5 Hz)

PREPARATION 5

The crystals of the following compound were obtained according to a similar manner to that of Preparation 4. 7-[2-(5-amino-1,2,4-thiadiazol-3-yl)-2-methoxyiminoacetamido]-3-(4-carbamoyl-1-quinuclidinio)-methyl-3-cephem-4-carboxylate sulfate (syn isomer)

mp: 170°–175° C. (dec.)

IR (Nujol): 1800, 1660, 1620, 1550 cm$^{-1}$

NMR (DMSO-d$_6$, δ): 1.70–2.40 (6H, m), 3.00–4.80 (10H, m), 3.95 (3H, s), 5.28 (1H, d, J=5 Hz), 5.90 (1H, dd, J=5 Hz, 8 Hz), 7.0–7.5 (2H, m), 8.13 (2H, s), 9.60 (1H, d, J=8 Hz)

PREPARATION 6

1) To a suspension of 7-[2-allyloxyimino-2-(5-amino-1,2,4-thiadiazol-3-yl)acetamido]-3-(1-pyridinio)methyl-3-cephem-4-carboxylate (syn isomer) (6.87 g) in water (200 ml) was added 1 N hydrochloric acid (17.5 ml) at ambient temperature.

The aqueous solution was lyophilized to give colorless powder (6.4 g). The powder was dissolved in water (6.4 ml) and the solution was allowed to stand for 3 hours at ambient temperature. The precipitated cristals were collected by filtration, washed with cooled water and ethanol, and dried over phosphorus pentoxide in vacuo to a mixture of colorless crystals of anhydride and dihydrate of 7-[2-allyloxyimino-2-(5-amino-1,2,4-thiadiazol-3-yl)acetamido]-3-(1-pyridinio)methyl-3-cephem-4-carboxylate hydrochloride (syn isomer) (2.10 g).

mp: 175° C. (dec.)

IR (Nujol): 1755, 1705, 1655, 1605 cm$^{-1}$

NMR (DMSO-d$_6$, δ): 3.37, 3.60 (2H, ABq, J=18 Hz), 4.63 (2H, m), 5.00–5.27 (3H, m), 5.40 (1H, m), 5.60 (2H, m), 5.70–6.20 (2H, m), 8.00–8.40 (4H, m), 8.67 (1H, t, J=8 Hz), 9.10 (1H, d, J=5 Hz), 9.60 (1H, d, J=8 Hz)

Elemental Analysis

Found: C, 43.13; H, 3.88; N, 17.76; S, 11.85; Cl, 6.25;

2) The mixture of the crystals of anhydride and dihydrate of 7-[2-allyloxyimino-2-(5-amino-1,2,4-thiadiazol-3-yl)acetamido]-3-(1-pyridinio)methyl-3-cephem-4-carboxylate hydrochloride (syn isomer) (2 g) was allowed to stand for 3 days over saturated aqueous potassium nitrate to give the crystals of 7-[2-allyloxyimino-2-(5-amino-1,2,4- thiadiazol-3-yl)acetamido]-3-(1-pyridinio)-methyl-3-cephem- 4-carboxylate hydrochloride dihydrate (syn isomer) (2.07 g).

mp: 175° C. (dec)

IR (Nujol): 1755, 1705, 1655, 1605 cm$^{-1}$

NMR (DMSO-d$_6$, δ): 3.37, 3.60 (2H, ABq, J=18 Hz), 4.63 (2H, m), 5.00–5.27 (3H, m), 5.40 (1H, m), 5.60. (2H, m), 5.70–6.20 (2H, m), 8.00–8.40 (4H, m), 8.67 (1H, t, J=8 Hz), 9.10 (1H, d, J=5 Hz), 9.60 (1H, d, J=8 Hz)

Water content: 6.69% (Karl-Fischer method)

PREPARATION 7

A solution of 7-[2-(5-amino-1,2,4-thiadiazol-3-yl)-2-methoxyiminoacetamido]-3-(1-pyridinio)methyl-3-cephem-4-carboxylate (syn isomer) (2 g) in 2 N sulfuric acid (2.1 ml) was lyophilized to give powder. The powder was dissolved in water (2.41 ml), and the solution was allowed to stand for 12 hours at 5° C.

The precipitated crystals were collected by filtration and air-dried to give colorless crystals of 7-[2-(5-amino-1,2,4-thiadiazol-3-yl)-2-methoxyiminoacetamido]-3-(1-pyridinio)methyl-3-cephem-4-carboxylate sulfate (syn isomer) (0.65 g).

IR (Nujol): 1788, 1640, 1538 cm$^{-1}$

NMR (D$_2$O, δ): 8.98 (2H, d, J=6 Hz), 8.63 (1H, t, J=7 Hz), 8.14 (2H, t, J=6 Hz), 5.96 (1H, d, J=5 Hz), 5.89–5.32 (2H, dd, J=15 Hz), 5.34 (1H, d, J=5 Hz), 4.08 (3H, s), 3.86–3.38 (2H, dd, J=18 Hz)

PREPARATION 8

The crystals of 7-[2-allyloxyimino-2-(5-amino-1,2,4-thiadiazol-3-yl)acetamido]-3-(1-pyridinio)methyl-3-cephem-4-carboxylate hydrochloride dihydrate (syn isomer) (10 g) was dried over phosphorus pentoxide under reduced pressure to give the crystals of 7-[2-allyloxyimino-2-(5-amino-1,2,4-thiadiazol-3-yl)acetamido]-3-(1-pyridinio)-methyl-3-cephem-4-carboxylate hydrochloride (syn isomer) (9.4 g).

mp: 175° C. (dec.)

IR (Nujol): 3400, 3275, 3175, 2200, 1790, 1700, 1660, 1025, 1015 cm$^{-1}$

NMR (DMSO-d$_6$, δ): 3.47 (2H, m), 4.63 (2H, m), 5.00–5.27 (3H, m), 5.40 (1H, m), 5.60 (2H, m), 5.70–6.20 (2H, m), 8.00–8.40 (4H, m), 8.67 (1H, t, J=8 Hz), 9.10 (1H, d, J=5 Hz), 9.60 (1H, d, J=8 Hz)

PREPARATION 9

The crystals of 7-[2-(5-amino-1,2,4-thiadiazol-3-yl)-2-propyloxyiminoacetamido]-3-(1-pyridinio)methyl-3-cephem-4-carboxylate hydrochloride dihydrate (syn isomer) were obtained according to a similar manner to that of Preparation 6.

IR (Nujol): 1760, 1705, 1660, 1615, 1590, 1540, 1520 cm$^{-1}$

NMR (D$_2$O-NaOD, δ): 0.90 (3H, t, J=8 Hz), 1.70 (2H, m), 3.17, 3.63 (2H, ABq, J=18 Hz), 4.20 (2H, t, J=8 Hz), 5.23 (1H, d, J=5 Hz), 5.28, 5.55 (2H, ABq, J=15 Hz), 5.85 (1H, d, J=5 Hz), 8.00 (2H, t, J=7 Hz), 8.50 (1H, t, J=7 Hz), 8.90 (2H, d, J=7 Hz)

Water content: 7.94% (Karl-Fisher method)

PREPARATION 10

7-[2-Allyloxyimino-2-(5-amino-1,2,4-thiadiazol-3-yl)-acetamido]-3-(1-pyridinio)methyl-3-cephem-4-carboxylate (syn isomer) (9.1 g) was dissolved with water (18 ml). The solution was stood for 4 hours at ambient temperature. The precipitated crystals were collected by filtration, washed with cold water, and dried over phosphorus pentoxide in vacuo to give colorless crystals of the above compound.

mp: 205°–210° C. (dec.)

IR (Nujol): 1795, 1660, 1640, 1620 cm$^{-1}$

NMR (DMSO-d$_6$-D$_2$O, δ): 3.02, 3.46 (2H, J=18 Hz), 4.62 (2H, m), 5.06 (1H, d, J=5 Hz), 5.10–5.50 (4H, m), 5.71 (1H, d, J=5 Hz), 5.80–6.00 (1H, m), 7.94 (2H, t, J=6 Hz), 8.44 (1H, t, J=6 Hz), 8.90 (1H, d, J=6 Hz)

PREPARATION 11

7-[2-(5-Amino-1,2,4-thiadiazol-3-yl)-2-methoxyiminoacetamido]-3-(1-pyridinio)methyl-3-cephem-4-carboxylate (syn isomer) (2 g) was dissolved in water (1 ml), and the solution was stood for 1 hour in refrigerator to give colorless crystals. Filtration and washing with acetone followed by ether gave colorless crystals of the above compound.

IR (Nujol): 1780, 1670, 1610 cm$^{-1}$

NMR (DMSO-d$_6$-D$_2$O, δ): 9.30 (2H, d, J=6 Hz), 8.61 (1H, t, J=7 Hz), 8.14 (2H, t, J=7 Hz), 5.80–5.53 (2H, m), 5.30–5.03 (2H, m), 3.93 (3H, s), 3.67–2.97 (2H, dd, J=17 Hz)

PREPARATION 12

1) 7-[2-allyloxyimino-2-(5-amino-1,2,4-thiadiazol-3-yl)-acetamido]-3-(1-pyridinio)methyl-3-cephem-4-carboxylate (syn isomer) (4 g) was dissolved in 0.2 N sulfuric acid (40 ml). The mixture was lyophilized to give 7-[2-allyloxyimino-2-(5-amino-1,2,4-thiadiazol-3-yl)-acetamido]-3-(1-pyridinio)methyl-3-cephem-4-carboxylate hemisulfate (syn isomer) (4.1 g).

IR (Nujol): 1770, 1640, 1620 cm$^{-1}$

NMR (DMSO-d$_6$,δ): 3.20, 3.50 (2H, ABq, J=18 Hz), 4.60 (2H, m), 5.00–5.60 (4H, m), 5.10 (1H, d, J=5 Hz), 5.70–6.10 (1H, m), 5.77 (1H, dd, J=5 Hz, 8 Hz), 8.00–8.30 (4H, m), 8.60 (1H, t, J=7 Hz), 9.15 (2H, d, J=7 Hz), 9.55 (1H, d, J=8 Hz)

2) The crystals of 7-[2-allyloxyimino-2-(5-amino-1,2,4-thiadiazol-3-yl)acetamido]-3-(1-pyridinio)methyl-3-cephem-4-carboxylate hemisulfate (syn isomer) was obtained according to a similar manner to that of Preparation 10.

NMR (DMSO-d$_6$, δ): 3.20, 3.50 (2H, ABq, J=18 Hz), 4.60 (2H, m), 5.00–5.60 (4H, m), 5.10 (1H, d, J=5 Hz), 5.70–6.10 (1H, m), 5.77 (1H, dd, J=5 Hz, 8 Hz), 8.00–8.30 (4H, m), 8.60 (1H, t, J=7 Hz), 9.15 (2H, d, J=7 Hz), 9.55 (1H, d, J=8 Hz)

3) 7-[2-allyloxyimino-2-(5-amino-1,2,4-thiadiazol-3-yl)-acetamido]-3-(1-pyridinio)methyl-3-cephem-4-carboxylate (syn isomer) (5 g) was dissolved in 1 M sulfuric acid (5 ml) at ambient temparature. Isopropyl alcohol (50 ml) was added to the mixture. The mixture was stirred for 2 hours at ambient temparature. The precipitated crystals were collected by filtration, washed with isopropyl alcohol, and dried over phosphorus pentoxide in vacuo to give the crystals of 7-[2-allyloxyimino-2-(5-amino-1,2,4-thiadiazol-3-yl)acetamido]-3-(1-pyridinio)-methyl-3-cephem-4-carboxylate hemisulfate (solvate of ½ isopropyl alcohol) (syn isomer) (5 g).

IR (Nujol): 1775, 1640, 1620 cm$^{-1}$

NMR (DMSO-d$_6$,δ): 1.15 (3H, d, J=6 Hz), 3.23, 3.70 (2H, ABq, J=18 Hz), 4.00 (0.5H, m), 4.70 (2H, m), 5.00–5.50 (5H, m), 5.50–6.20 (2H, m), 8.07 (2H, t, J=7 Hz), 8.57 (1H, t, J=8 Hz), 8.93 (2H, d, J=7 Hz) (1H, d, J=Hz),

PREPARATION 13

1) 7-[2-allyloxyimino-2-(5-amino-1,2,4-thiadiazol-3-yl)-acetamido]-3-(1-pyridinio)methyl-3-cephem-4-carboxylate (syn isomer) (4 g) was dissolved in 0.4 N sulfuric acid (40 ml). The mixture was lyophilized to give 7-[2-allyloxyimino-2-(5-amino-1,2,4-thiadiazol-3-yl)-acetamido]-3-(1-pyridinio)methyl-3-cephem-4-carboxylate sulfate (syn isomer) (4.20 g).

IR (Nujol): 1770, 1640, 1620 cm$^{-1}$

NMR (DMSO-d$_6$,δ): 3.20, 3.50 (2H, ABq, J=18 Hz), 4.60 (2H, m), 5.00–5.60 (4H, m), 5.10 (1H, d, J=5 Hz), 5.70–6.10 (1H, m), 5.77 (1H, dd, J=5 Hz, 8 Hz), 8.00–8.30 (4H, m), 8.60 (1H, t, J=7 Hz), 9.15 (2H, d, J=7 Hz), 9.55 (1H, d, J=8 Hz)

The crystals of 2) 7-[2-allyloxyimino-2-(5-amino-1,2,4-thiadiazol-3-yl)-acetamido]-3-(1-pyridinio)methyl-3-cephem-4-carboxylate sulfate (syn isomer) was obtained according to a similar manner to that of Preparation 10.

NMR (DMSO-d$_6$,δ): 3.20, 3.50 (2H, ABq, J=18 Hz), 4.60 (2H, m), 5.00–5.60 (4H, m), 5.10 (1H, d, J=5 Hz), 5.70–6.10 (1H, m), 5.77 (1H, dd, J=5 Hz, 8 Hz), 8.00–8 30 (4H, m), 8.60 (1H, t, J=7 Hz), 9.15 (2H, d, J=7 Hz), 9.55 (1H, d, J=8 Hz)

PREPARATION 14

7-[2-Allyloxyimino-2-(5-amino-1,2,4-thiadiazol-3-yl)-acetamido]-3-(1-pyridinio)methyl-3-cephem-4-carboxylate (syn isomer) (4 g) was dissolved in 0.2 N hydrochloric acid (40 ml). The mixture was lyophilized to give 7-[2-allyloxyimino-2-(5-amino-1,2,4-thiadiazol-3-yl)acetamido ]-3-(1-pyridinio)methyl-3-cephem-4-carboxylate hydrochloride (syn isomer) (4.0 g).

IR (Nujol): 1770, 1660, 1610 cm$^{-1}$

NMR (DMSO-d$_6$,δ): 3.30, 3.63 (2H, ABq, J=18 Hz), 4.60 (2H, m), 4.70–5.70 (8H, m), 5.70–6.10 (1H, m), 8.00–8.40 (4H, m), 8.60 (1H, t, J=7 Hz), 9.20 (2H, d, J=6 Hz), 9.60 (1H, d, J=8 Hz)

PREPARATIONS OF WATER-SOLUBLE ANTIBIOTIC COMPOSITIONS

EXAMPLE 1

| Components | mole equivalent |
| --- | --- |
| Compound A | 1 |
| Sodium carbonate | 1 |

The above-mentioned components were aseptically mixed, and the aseptic mixture was packed into sterilized dry vial to obtain a pharmaceutical preparation for injection.

the pharmaceutical preparations for injection comprising the following components were obtained according to a similar way to that of Example 1.

| Components | mole equivalent |
| --- | --- |
| Example 2 | |
| Compound A | 1 |
| Sodium hydrogencarbonate | 1 |
| Example 3 | |
| Compound A | 1 |
| Potassium carbonate | 1 |
| Example 4 | |
| Compound A | 1 |
| Potassium hydrogencarbonate | 2 |
| Example 5 | |
| Compound A | 1 |
| Sodium hydrogencarbonate | 2 |
| Example 6 | |
| Compound A | 1 |
| Ammonium carbonate | 2 |
| Example 7 | |
| Compound A | 1 |
| Ammonium hydrogencarbonate | 2 |
| Example 8 | |
| Compound B | 1 |
| Sodium carbonate | 1 |

| Components | mole equivalent |
| --- | --- |
| Example 9 | |
| Compound C | 1 |
| Sodium hydrogencarbonate | 1 |
| Example 10 | |
| Compound D | 1 |
| Sodium hydrogencarbonate | 3 |
| Example 11 | |
| Compound E | 1 |
| Sodium hydrogencarbonate | 1 |
| Example 12 | |
| Compound F | 1 |
| Sodium hydrogencarbonate | 2 |
| Example 13 | |
| Compound G | 1 |
| Sodium hydrogencarbonate | 3 |

PREPARATIONS OF THE SALTS OF NEW CEPHEM COMPOUND

EXAMPLE 14

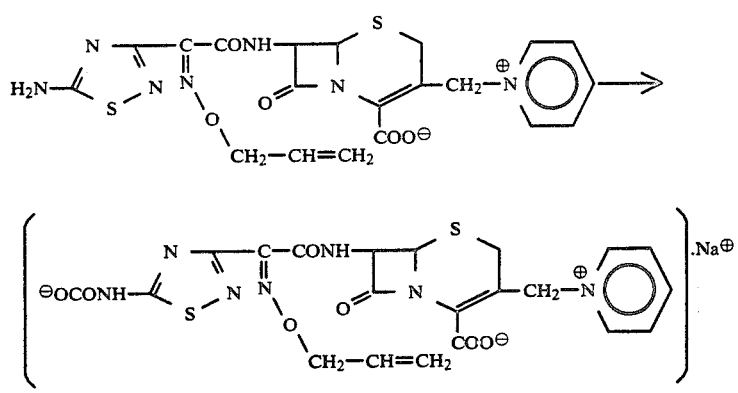

To a solution of 7-[2-allyloxyimino-2-(5-amino-1,2,4-thiadiazol-3-yl)acetamido]-3-(1-pyridinio)methyl-3-cephem-4-carboxylate (syn isomer) (1.15 g) in 50% aqueous acetone (9.2 ml) was added sodium hydrogencarbonate (193 mg) and dry ice (4.4 g) at room temperature. The mixture was stirred in a sealed tube for 5 hours. Acetone was removed under reduced pressure. The residual solution was chromatographed on non-ionic adsorption resin "Diaion HP-20" (Trademark, maker: Mitsubishi Chemical Industries) eluting with water. The desired fractions were collected and lyophilized to give sodium 7-[2-allyloxyimino-2-(5-carboxylatoamino-1,2,4-thiadiazol-3-yl)acetamido]-3-(1-pyridinio)methyl-3-cephem-4-carboxylate (syn isomer) (500 mg).

IR (Nujol): 3500–3100, 1765, 1660, 1610, 1530 cm$^{-1}$

NMR (DMSO-$d_6$, δ): 4.6 (2H, m), 5.10 (1H, d, J=5 Hz), 5.2 (2H, m), 5.33 and 5.53 (2H, ABq, J=12 Hz), 5.76 (1H, dd, J=5 Hz, 8 Hz), 5.8–6.2 (1H, m), 8.10 (2H, t, J=6 Hz), 8.55 (1H, m), 9.40 (3H, m), 10.1 (1H, brord s)

FAB Mass: m/z 569 (M+1)

EXAMPLE 15

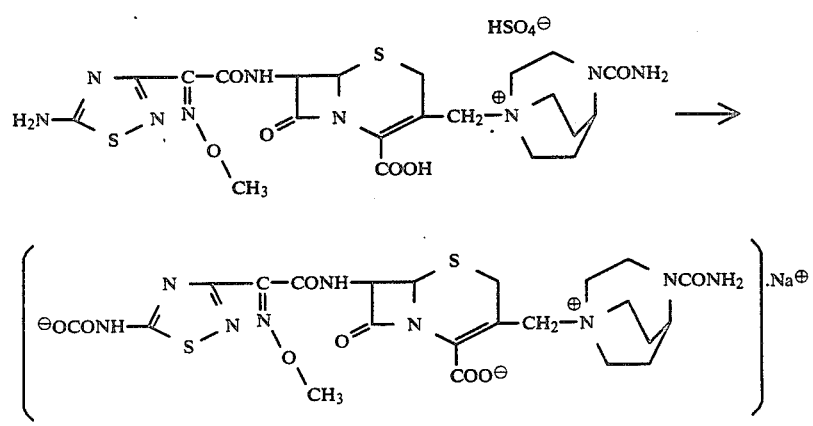

Sodium 7-[2-(5-carboxylatoamino-1,2,4-thiadiazol-3-yl)-2-methoxyiminoacetamido]-3-[4-carbamoyl-1,4-diazabicyclo[3.2.2]nonan-1-ylio]methyl-3-cephem-4-carboxylate (syn isomer) (463 mg) was obtained by reacting 7-[2-(5-amino-1,2,4-thiadiazol-3-yl)-2-methoxyiminoacetamido]-3-[4-carbamoyl-1,4-diazabicyclo[3.2.2]nonan-1-ylio]methyl-3-cephem-4-carboxylate sulfate (syn isomer) (1 g) with sodium hydrogencarbonate (379 mg) and dry ice (4 g) according to a similar manner to that of Example 14.

mp: 140° C. (dec.)

IR (Nujol): 1770, 1660, 1620 cm$^{-1}$

NMR ($D_2O$, δ): 2.0–2.6 (4H, m), 2.8–3.20 (1H, m), 3.25–4.25 (12H, m), 4.10 (3H, s), 5.35 (1H, d, J=5 Hz), 5.90 (1H, d, J=5 Hz)

NMR (DMSO-$d_6$, δ): 1.80–2.30 (4H, m), 2.70–4.40 (13H, m), 3.92 (3H, s), 5.10 (1H, d, J=5 Hz), 5.70 (1H, m), 6.12 (2H, m), 9.50 (1H, m), 9.90 (1H, s)

EXAMPLE 16

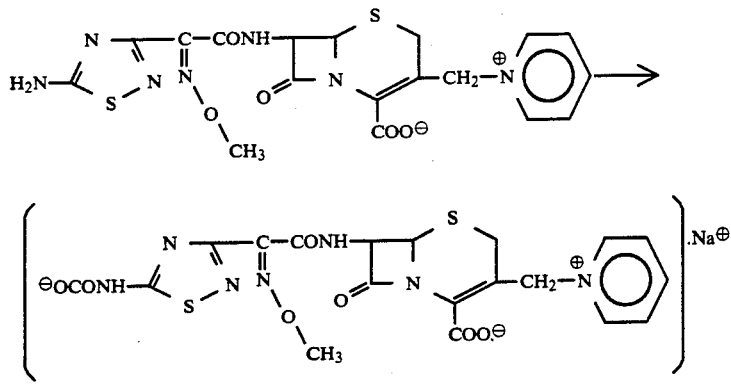

Sodium 7-[2-(5-carboxylatoamino-1,2,4-thiadiazol-3-yl)-2-methoxyiminoacetamido]-3-(1-pyridinio)methyl-3-cephem- 4-carboxylate (syn isomer) (550 mg) was obtained by reacting 7-[2-(5-amino-1,2,4-thiadiazol-3-yl)-2-methoxyiminoacetamido]-3-(1-pyridinio)methyl-3-cephem-4-carboxylate (syn isomer) (2.09 g) with sodium hydrogencarbonate (1.11 g) and dry ice (8.36 g) according to a similar manner to that of Example 14.

IR (Nujol): 1755 cm$^{-1}$

NMR (DMSO-d$_6$, δ): 9.78 (1H, s), 9.47 (2H, d, J=6 Hz), 8.59 (1H, t, J=7 Hz), 8.16 (2H, t, J=6 Hz), 5.82–5.03 (3H, m), 5.06 (1H, d, J=7 Hz), 3.86 (3H, s), 3.63–2.92 (2H, dd, J=18 Hz)

EXAMPLE 17

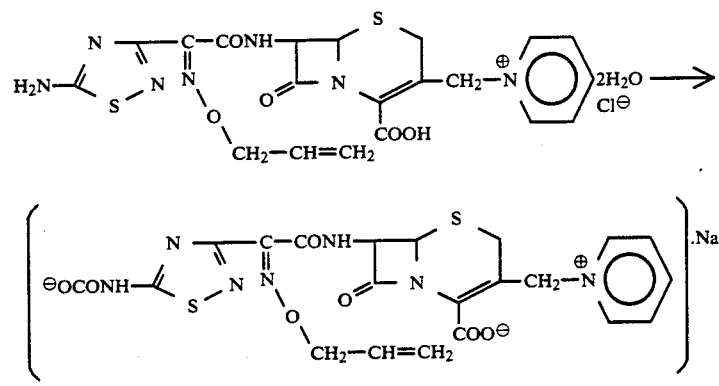

To a mixture of 7-[2-allyloxyimino-2-(5-amino-1,2,4-thiadiazol-3-yl)acetamido]-3-(1-pyridinio)methyl-3-cephem-4-carboxylate hydrochloride dihydrate (syn isomer) (50 mg) and sodium hydrogencarbonate (14.6 mg) was added water (0.25 ml) at ambient temperature. Carbon dioxide was generated and the mixture became homogeneous solution.

The solution was subjected to high performance liquid chromatography. Elution was carried out using a column (4 mmØ×25 cm) with "Lichrosorb RP-18" (Trademark, maker; Merk & Co) as a carrier and a mixture of acetonitrile and 16.4 mM phosphate buffer (pH 7) (1:9 V/V) as a mobile phase under flow rate of 1 ml/minute.

Sodium 7-[2-allyloxyimino-2-(5-carboxylatoamino-1,2,4-thiadiazol-3-yl)acetamido]-3-(1-pyridinio)methyl-3-cephem-4-carboxylate (syn isomer) was detected by monitoring with UV detector at 254 nm.

EXAMPLE 18

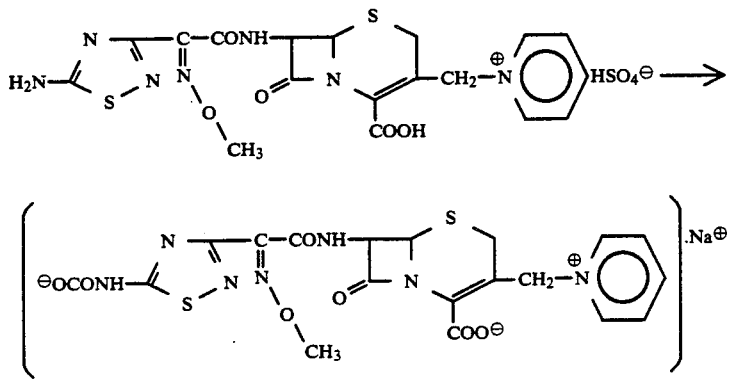

Sodium 7-[2-(5-carboxylatoamino-1,2,4-thiadiazol-3-yl)-2-methoxyiminoacetamido]-3-(1-pyridinio)methyl-3-cephem-4-carboxylate (syn isomer) was prepared by reacting 7-[2-(5-amino-1,2,4-thiadiazol-3-yl)-2-methoxyiminoacetamido]-3-(1-pyridinio)methyl-3-cephem-4-carboxylate sulfate (syn isomer) (50 mg) and sodium hydrogencarbonate (22 mg) and detected according to a similar manner to that of Example 17.

EXAMPLE 19

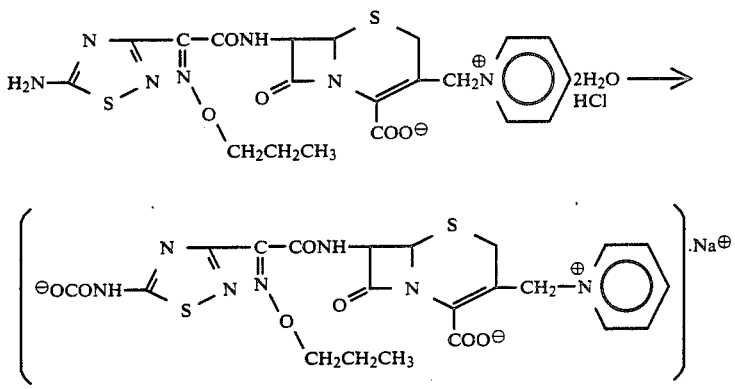

Sodium 7-[2-(5-carboxylatoamino-1,2,4-thiadiazol-3-yl)-2-propyloxyiminoacetamido]-3-(1-pyridinio)methyl-3-cephem-4-carboxylate (syn isomer) (141.5 mg) was obtained by reacting 7-[2-(5-amino-1,2,4-thiadiazol-3-yl)-2-propyloxyiminoacetamido]-3-(1-pyridinio)methyl-3-cephem-4-carboxylate hydrochloride dihydrate (syn isomer) (100 mg) and sodium hydrogencarbonate (29 mg) according to a similar manner to that of Example 17.

NMR (DMSO-$d_6$, δ): 0.87 (3H, t, J=8 Hz), 1.63 (2H, m), 3.04, 3.56 (2H, ABq, J=17 Hz), 4.02 (2H, t, J=6 Hz), 5.05 (1H, d, J=5 Hz), 5.17, 5.68 (2H, ABq, J=13 Hz), 8.10 (3H, m), 8.53 (1H, t, J=8 Hz), 9.40 (2H, m), 9.83 (1H, s)

EXAMPLE 20

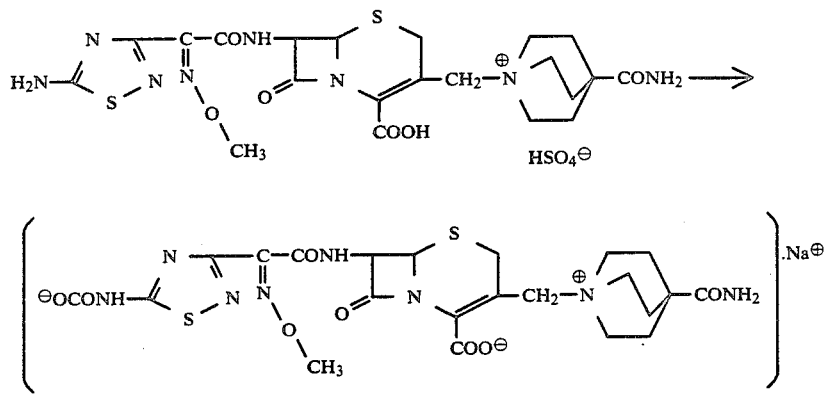

To a suspension of crystals of 7-[2-(5-amino-1,2,4-thiadiazol-3-yl)-2-methoxyiminoacetamido]-3-(4-carbamoyl-1-quinuclidinio)methyl-3-cephem-4-carboxylate sulfate (syn isomer) (500 mg) in 50% aqueous acetone (4 ml) was added sodium hydrogencarbonate (323 mg) at ambient temperature. Carbonic acid gas was bubbled into the mixture for four hours and diluted with water. The resulting mixture was chromatographed on non-ionic adsorption resin "Diaion HP-20" (50 ml) eluting with water. The desired fractions were collected and lyophilized to give sodium 7-[2-(5-carboxylatoamino-1,2,4-thiadiazol-3-yl)-2-methoxyiminoacetamido]-3-(4-carbamoyl-1-quinuclidinio)-methyl-3-cephem-4-carboxylate (syn isomer) (239.6 mg).

IR (Nujol): 1765, 1650, 1610, 1530 cm$^{-1}$
NMR (DMSO-$d_6$, δ): 1.70-2.20 (6H, m), 3.0-4.0 (10H, m), 3.90 (3H, s), 5.10 (1H, d, J=5 Hz), 5.67 (1H, m), 7.00-7.50 (2H, m), 9.25-9.65 (1H, m), 9.98 (1H, s)

EXAMPLE 21

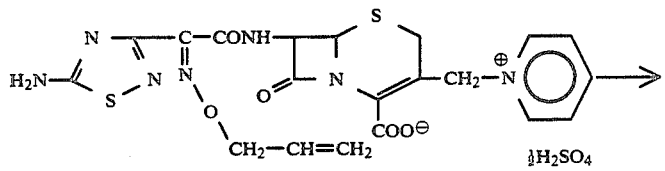

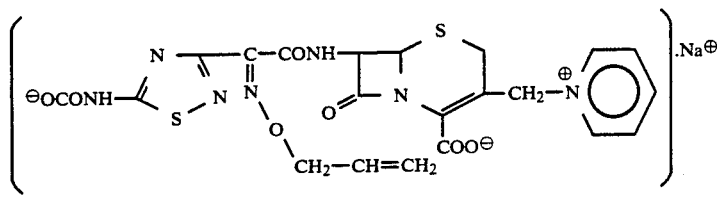

Sodium 7-[2-(5-carboxylatoamino-1,2,4-thiadiazol-3-yl)-2-allyloxyiminoacetamido]-3-(1-pyridinio)methyl-3-cephem-4-carboxylate (syn isomer) was prepared by reacting 7-[2-(5-amino-1,2,4-thiadiazol-3-yl)-2-allyloxyiminoacetamido]-3-(1-pyridinio)methyl-3-cephem-4-carboxylate hemisulfate (syn isomer) (50 mg) and sodium hydrogencarbonate (15.3 mg) and detected according to a similar manner to that of Example 17.

EXAMPLE 22

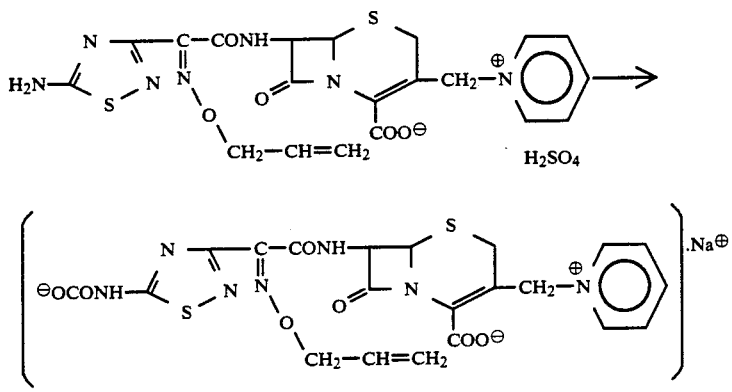

Sodium 7-[2-(5-carboxylatoamino-1,2,4-thiadiazol-3-yl)-2-allyloxyiminoacetamido]-3-(1-pyridinio)methyl-3-cephem-4-carboxylate (syn isomer) was prepared by reacting 7-[2-(5-amino-1,2,4-thiadiazol-3yl)-2-allyloxyiminoacetamido]-3-(1-pyridinio)methyl-3-cephem-4-carboxylate sulfate (syn isomer) (50 mg) and sodium hydrogencarbonate (21 mg) and detected according to a similar manner to that of Example 17.

EXAMPLE 23

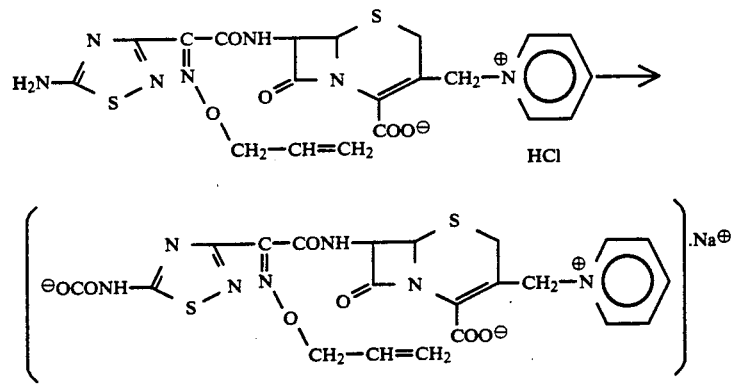

Sodium 7-[2-(5-carboxylatoamino-1,2,4-thiadiazol-3-yl)-2-allyloxyiminoacetamido]-3-(1-pyridinio)methyl-3-cephem-4-carboxylate (syn isomer) was prepared by reacting 7-[2-(5-amino-1,2,4-thiadiazol-3yl)-2-allyloxyiminoacetamido]-3-(1-pyridinio)methyl-3-cephem-4-carboxylate hydrochloride (syn isomer) (50 mg) and sodium hydrogencarbonate (15.6 mg) and detected according to a similar manner to that of Example 17.

What we claim is:

1. A water-soluble antibiotic composition which comprises crystals of a cephem compound of the following formula:

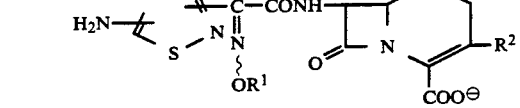

wherein $R^1$ is lower alkyl or lower alkenyl, each of which may have substituent(s) selected from the group consisting of carboxy, halogen, cyano, amino and hydroxy, and $R^2$ is lower alkyl substituted with a 5 - to 10-membered mono or bicyclic heterocyclic group containing a quaternary nitrogen atom which may have a carbamoyl group, or an acid addition salt thereof, and a pharmaceutically acceptable carbonic acid salt.

2. A water-soluble antibiotic composition of the claim 1, wherein the cephem compound is in a form of the acid addition salt.

3. A water-soluble antibiotic composition of the claim 2, wherein the ratio of the acid addition salt of the cephem compound to the carbonic acid salt is 1:0.5 to 1:4 equivalents.

4. A water-soluble antibiotic composition of the claim 3, wherein the ratio of the acid addition salt of the cephem compound to the carbonic acid salt is 1:1 to 1:3 equivalents.

5. A water-soluble antibiotic composition of the claim 4, wherein $R^1$ is lower alkyl or lower alkenyl, $R^2$ is 1-pyridiniomethyl, and the pharmaceutically acceptable carbonic acid salt is alkaline metal hydrogencarbonate or alkaline metal carbonate.

6. A water-soluble antibiotic composition of the claim 5, wherein $R^1$ is allyl or propyl.

7. A water-soluble antibiotic composition of the claim 6, wherein the acid addition salt of the cephem compound is 7-[2-allyloxyimino-2-(5-amino-1,2,4-thiadiazol-3yl)-acetamido]-3-(1-pyridinio)methyl-3-cephem-4-carboxylate hydrochloride (syn isomer) or its dihydrate.

8. A water-soluble antibiotic composition of the claim 7, wherein alkaline metal hydrogencarbonate is sodium hydrogencarbonate, and the ratio of the acid addition salt of the cephem compound to sodium hydrogencarbonate is 1:1 equivalent.

9. A salt comprising cation(s) and anion of the formula:

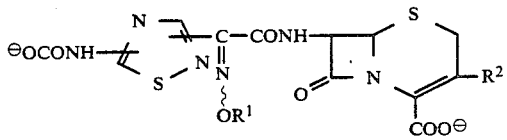

wherein $R^1$ is lower alkyl or lower alkenyl, each of which may have substituent(s) selected from the group consisting of carboxy, halogen, cyano, amino and hydroxy, and $R^2$ is lower alkyl substituted with a 5- to 10-membered mono or bicyclic heterocyclic group containing a quaternary nitrogen atom which may have a carbamoyl group.

10. A salt of the claim 9, wherein the anion is represented by the following formula:

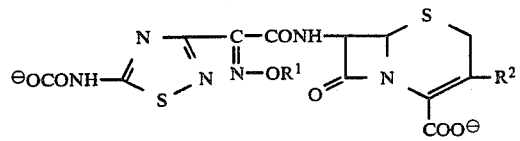

wherein $R^1$ is lower alkyl or lower alkenyl and $R^2$ is 1-pyridiniomethyl, quinuclidiniomethyl, or a group of the formula:

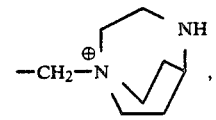

each of which may have carbamoyl.

11. A salt of the claim 10, wherein $R^2$ is 1-pyridiniomethyl, and the cation is an alkaline metal.

12. A salt of the claim 11, which is sodium 7-[2-allyloxyimino-2-(5-carboxylatoamino-1,2,4-thiadiazol-3-yl)acetamido]-3-(1-pyridinio)methyl-3-cephem-4-carboxylate (syn isomer).

13. A salt of the claim 11, which is sodium 7-[2-(5-carboxylatoamino-1,2,4-thiadiazol-3-yl)-2-propyloxyiminoacetamido]-3-(1-pyridinio)methyl-3-cephem-4-carboxylate (syn isomer).

14. An antibiotic, pharmaceutical composition comprising an effective amount of a salt of claim 9 in association with a pharmaceutically acceptable, substantially non-toxic carrier or excipient.

15. A method for the treatment of infectious diseases caused by pathogenic bacteria which comprises administering an antibiotically effective amount of a salt of claim 9 to a human or animal.

* * * * *